United States Patent
Mao et al.

(10) Patent No.: US 10,870,790 B2
(45) Date of Patent: Dec. 22, 2020

(54) TRI-CATIONIC VISCOELASTIC SURFACTANT, PREPARATION METHOD AND APPLICATION THEREOF AND CLEAN FRACTURING FLUID

(71) Applicant: Southwest Petroleum University, Chengdu (CN)

(72) Inventors: Jincheng Mao, Chengdu (CN); Jinming Fan, Guang'an (CN); Jinzhou Zhao, Chengdu (CN); Xiaojiang Yang, Chengdu (CN)

(73) Assignee: SOUTHWEST PETROLEUM UNIVERSITY, Chengdu (CN)

( * ) Notice: Subject to any disclaimer, the term of this patent is extended or adjusted under 35 U.S.C. 154(b) by 369 days.

(21) Appl. No.: 16/068,134

(22) PCT Filed: Jan. 29, 2018

(86) PCT No.: PCT/CN2018/074502
§ 371 (c)(1),
(2) Date: Jul. 5, 2018

(87) PCT Pub. No.: WO2019/136782
PCT Pub. Date: Jul. 18, 2019

(65) Prior Publication Data
US 2020/0283676 A1 Sep. 10, 2020

(30) Foreign Application Priority Data
Jan. 11, 2018 (CN) .................. 2018 1 00275036

(51) Int. Cl.
| | | |
|---|---|---|
| C09K 8/68 | (2006.01) | |
| C07C 231/12 | (2006.01) | |
| C07C 233/36 | (2006.01) | |
| C07C 233/38 | (2006.01) | |
| C07C 235/74 | (2006.01) | |

(52) U.S. Cl.
CPC .............. *C09K 8/68* (2013.01); *C07C 231/12* (2013.01); *C07C 233/36* (2013.01); *C07C 233/38* (2013.01); *C07C 235/74* (2013.01); *C09K 2208/30* (2013.01)

(58) Field of Classification Search
CPC .... C09K 8/68; C09K 2208/30; C07C 233/36; C07C 231/12; C07C 233/38; C07C 235/74
See application file for complete search history.

(56) References Cited

FOREIGN PATENT DOCUMENTS

| | | | |
|---|---|---|---|
| CN | 103951599 A | | 7/2014 |
| CN | 103965861 | * | 8/2014 |
| CN | 103965861 A | | 8/2014 |
| CN | 104645876 A | | 5/2015 |
| CN | 105688738 A | | 6/2016 |
| CN | 105688739 A | | 6/2016 |
| JP | 2017052724 | * | 3/2017 |

OTHER PUBLICATIONS

Jincheng Mao et al. "Development and Performance Evaluation of High Temperature Resistant Clean Fracturing Fluid System HT-160". Petroleum Drilling Techniques. Nov. 30, 2017. 45(6): 105-109.

* cited by examiner

Primary Examiner — Kumar R Bhushan
(74) Attorney, Agent, or Firm — Bayramoglu Law Offices LLC

(57) ABSTRACT

A three-poly cationic viscoelastic and a clean fracturing fluid containing the three-poly cationic viscoelastic surfactant are provided. N, N'-dimethyl-1,3-propanediamine and epichlorohydrin are used to prepare an intermediate A, and then the intermediate A and a fatty acid amidopropyl dimethylamine is used to prepare the three-poly cationic viscoelastic surfactant. The preparation process is simple. The clean fracturing fluid including the three-poly cationic viscoelastic surfactant has excellent temperature and shear resistance, strong suspended sand performance, simple on-site preparation, automatic gel breaking, small damage to formation, low cost and simple preparation process. The clean fracturing fluid including the surfactant also has strong temperature resistance, and the viscosity of the product can be maintained at 42 mPa·s after 80 minutes at 180° C. and 170 $s^{-1}$, which is higher than the viscosity requirement (>25 mPa·s) of the clean fracturing fluid in on-site construction.

15 Claims, 4 Drawing Sheets

TRI-CATIONIC VISCOELASTIC SURFACTANT, PREPARATION METHOD AND APPLICATION THEREOF AND CLEAN FRACTURING FLUID

CROSS REFERENCE TO RELATED APPLICATIONS

This application is the national phase entry of International Application PCT/CN2018/074502, filed on Jan. 29, 2018, which is based upon and claims priority to Chinese Patent Application No. 2018100275036, filed on Jan. 11, 2018, the entire contents of which are incorporated herein by reference.

TECHNICAL FIELD

The present invention relates to the technical field of fracturing fluid for oil reservoirs, in particular to a tri-cationic viscoelastic surfactant, a preparation method and an application thereof and a clean fracturing fluid.

BACKGROUND

With the rapid development in oil-gas exploration, a large number of unconventional oil-gas reservoirs have been discovered. The difficulty of exploitation of such reservoirs is far greater than that of conventional reservoirs. After nearly 70-year development, hydraulic fracturing technology has gradually become one of the main measures to improve the production efficiency of oil-gas fields. In hydraulic fracturing, the performance of fracturing fluid has a great effect on the whole construction process. Therefore, the way to improve the performance of fracturing fluid has attracted extensive attention at home and abroad.

Viscoelastic surfactant (VES) fracturing fluid, commonly known as a clean fracturing fluid in the industry, was first proposed by Schlumberger in 1997 and successfully applied in fracturing operation. VES fracturing fluid is prepared by compounding viscoelastic surfactant as thickening agent and organic salt or inorganic salt as a counter-ion. Under the action of counter-ions, surfactants in the solution form rod-like or worm-like structures and are intertwined to each other to form a three-dimensional network structure, which also makes the crosslinking agent unnecessary in the preparation of VES fracturing fluid. Compared with water-based fracturing fluid system using guar gum as a main thickening agent, the VES fracturing fluid has many advantages, for example: 1. the on-site preparation work is easy, without a need for the crosslinking agent; 2. the VES fracturing fluid has low friction, good viscoelasticity and good sand-carrying performance; 3. the surfactant has a low molecular weight, which makes it easy for flowback, and the gel breaking can be conducted by contacting with the hydrocarbon fluid in the formation without gel breaker; 4. the VES fracturing fluid does not form a filter cake and does little damage to the formation. So the VES fracturing fluid is applied in many fields and processes of production stimulation of oil-gas fields.

The VES fracturing fluid has been used in a large number of fracturing operations in foreign countries, but it is seldom studied and used in China. The main reasons are: (1) the cost is high, because of the complex preparation process and large dosage of thickening agent, the usage cost of VES fracturing fluid is nearly 10 times higher than that of guar gum and polymer fracturing fluid; (2) the usage effect of the VES fracturing fluid is not ideal at high temperatures, and the VES fracturing fluid is usually operated at well temperature below 120° C., so the VES fracturing fluid cannot cope with the development of ultra-deep and ultra-high temperature oil and gas reservoirs. Therefore, it is of great practical significance to develop a VES fracturing fluid with high temperature resistance and low price.

SUMMARY

The objective of the present invention is to provide a tri-cationic viscoelastic surfactant, a preparation method and application thereof, and a clean fracturing fluid including the tri-cationic viscoelastic surfactant, so as to solve the problems of complex preparation process, high production cost and poor high temperature resistance of the existing thickening agent of the fracturing fluid.

In order to solve the above-mentioned technical problem, the technical solution of the present invention is as follows.

A tri-cationic viscoelastic surfactant has the following structural formula:

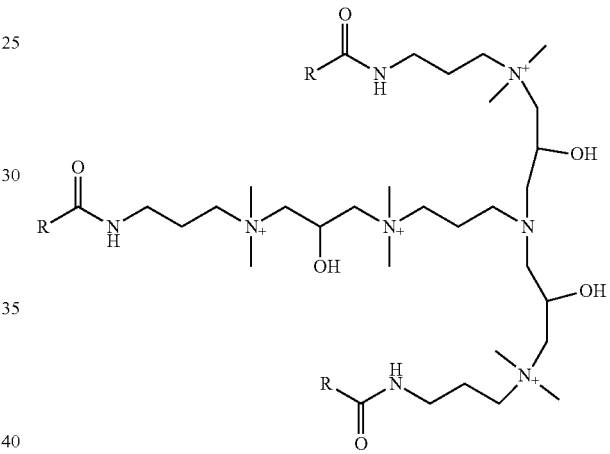

R is a saturated or unsaturated hydrocarbon chain with 17 to 21 carbon atoms.

The molecular formula of the tri-cationic viscoelastic surfactant is $R_3C_{32}H_{69}N_8O_6$. The number of carbon atoms of R can be 17 or 21.

Further, in a preferred embodiment of the present invention, R is a hydrophobic carbon chain of erucic acid, oleic acid or stearic acid.

The structural formula of the hydrophobic carbon chain of erucic acid is as follows:

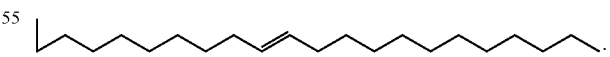

The structural formula of the hydrophobic carbon chain of oleic acid is as follows:

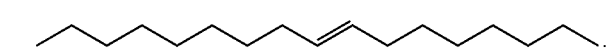 [SMILES: CCCCCCC/C=C/CCCCCCCC]

The structural formula of the hydrophobic carbon chain of stearic acid is as follows:

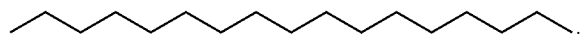 [SMILES: CCCCCCCCCCCCCCCCC]

The preparation method of the above-mentioned tri-cationic viscoelastic surfactant includes the following steps:

(1) dissolving N,N'-dimethyl-1,3-propanediamine in an organic solvent, adding epichlorohydrin and concentrated hydrochloric acid, performing a reflux reaction for 5-7 hours at 55-65° C., and then performing a distillation under reduced pressure and performing an extraction to obtain an intermediate A; a molar ratio of the N,N'-dimethyl-1,3-propanediamine to the epichlorohydrin to the concentrated hydrochloric acid is 1:(3-6):(1-1.5);

(2) dissolving the intermediate A in an organic solvent, adding fatty acid amidopropyl dimethylamine, stirring and performing a reflux reaction for 11-13 h at 80-90° C. and 250-300 r/min, and then performing a distillation under reduced pressure to obtain the tri-cationic viscoelastic surfactant; a molar ratio of intermediate A to the fatty acid amidopropyl dimethylamine is 1:(3-3.1); in the step (1), intermediate A is prepared by using N,N'-dimethyl-1,3-propanediamine and epichlorohydrin in the present invention. The reaction process is as follows:

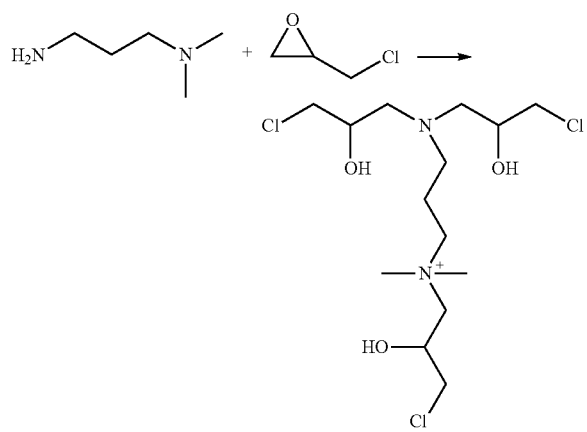

In the process of the reaction, epichlorohydrin is ring-opened and then attached to the two N atoms of N,N'-dimethyl-1,3-propanediamine to obtain intermediate A. According to the present invention, the reaction conditions of this step are controlled at 60° C. for 6 h. Under the condition, the yield of intermediate A is the highest, thus ensuring the yield of the surfactant of the final product. Moreover, the reaction can be promoted to proceed efficiently at 60° C., avoiding the low yield of intermediate A caused by low reaction activity at lower temperature and the generation of by-products which affect the purity of products at higher temperature. Because when the temperature is too high (above 60° C.), by-products will be generated due to the quaternization of Cl of epichlorohydrin with the tertiary amine group of N,N'-dimethyl-1,3-propanediamine.

The molar ratio of above-mentioned N,N'-dimethyl-1,3-propanediamine to the epichlorohydrin to the concentrated hydrochloric acid is preferably 1:3:1, 1:3.3:1, 1:6:1.5 or 1:3:1.2.

The reaction process of intermediate A and fatty acid amidopropyl dimethylamine in step (2) is as follows:

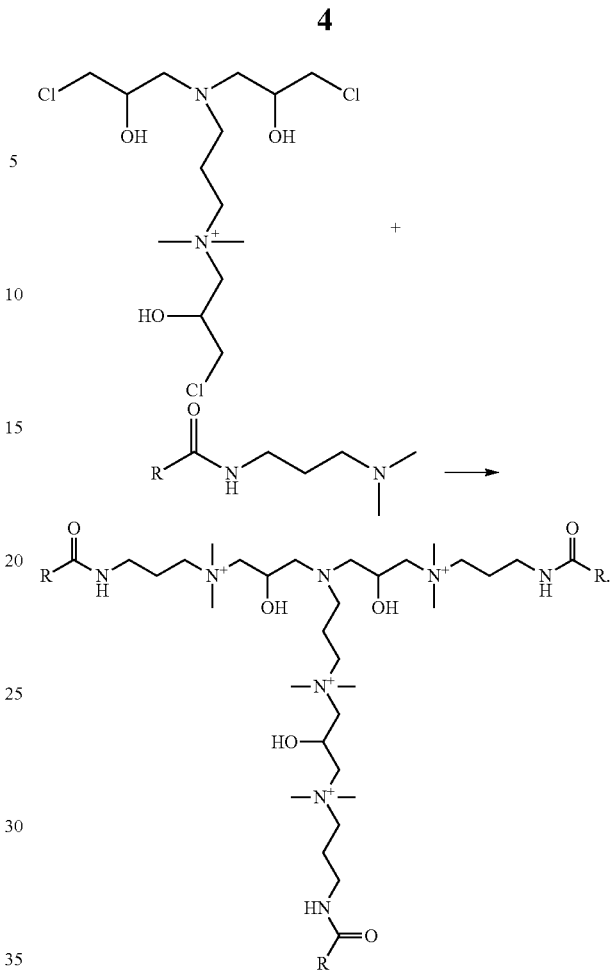

In the process of the reaction, three Cl at the tail ends of the three chains of intermediate A are subjected to a quaternization reaction with the tertiary amino group of the fatty acid amidopropyl dimethylamine to obtain the final product: a tri-cationic viscoelastic surfactant. According to the present invention, the reaction conditions of this step are controlled at 85° C. for 12 hours to obtain the highest product yield. Moreover, the quaternization reaction can be fully performed at 85° C. to avoid the situations that the quaternization reaction is insufficient due to low temperature, and quaternization reaction cannot occur at all tail ends of the three chains of intermediate A, thus generating by-products and affecting the product quality.

The whole preparation process of the present invention is performed in two steps. Intermediate A is preferentially prepared, thus ensuring the yield of the tri-cationic viscoelastic surfactant of the final product, simultaneously reducing the generation of by-products and ensuring the quality of the final product. According to the present invention, N,N'-dimethyl-1,3-propanediamine and epichlorohydrin are used as reactants, and an intermediate A of linking group with three chains and Cl at the tail ends of the chains can be obtained through ring opening reaction. Then, three Cl at the tail ends of the three chains are subjected to a quaternization reaction with tertiary amine groups of fatty acid amidopropyl dimethylamine, and finally a molecule with three single chain surfactants are obtained, thus the tri-cationic viscoelastic surfactant is obtained.

The above-mentioned preparation method includes the following steps:

(1) dissolving N,N'-dimethyl-1,3-propanediamine in ethanol, adding epichlorohydrin and concentrated hydrochloric acid, performing the reflux reaction at 60° C. for 6 hours, and then performing the distillation under reduced pressure and performing the extraction to obtain an intermediate A. A molar ratio of the N,N'-dimethyl-1,3-propanediamine to the epichlorohydrin to the concentrated hydrochloric acid is 1:3.3:1;

(2) dissolving intermediate A in ethanol, adding fatty acid amidopropyl dimethylamine, stirring and performing the reflux reaction for 12 h at 85° C. and 250-300 r/min, and then performing the distillation under reduced pressure to obtain the tri-cationic viscoelastic surfactant. A molar ratio of intermediate A to the fatty acid amidopropyl dimethylamine is 1:3.

Further, in the preferred embodiment of the present invention, the fatty acid amidopropyl dimethylamine is a combination of one or more of erucamide propyl dimethylamine, oleic amide propyl dimethylamine and stearic amide propyl dimethylamine.

Further, in the preferred embodiment of the present invention, the above-mentioned organic solvent is ethanol or isopropanol.

An application of the above-mentioned tri-cationic viscoelastic surfactant is to prepare a clean fracturing fluid.

A clean fracturing fluid includes a counter-ion salt and a tri-cationic viscoelastic surfactant prepared by the above-mentioned preparation method. Further, in a preferred embodiment of the present invention, the clean fracturing fluid includes 1-3 wt % of a tri-cationic viscoelastic surfactant, 1-1.4 wt % of a counter-ion salt and the rest of the clean fracturing fluid is water.

Preferably, the weight ratio of the tri-cationic viscoelastic surfactant is 1 wt %, 2 wt % or 3 wt %.

Preferably, the weight ratio of the counter-ion salt is 1 wt %, 1.2 wt % or 1.4 wt %.

Further, in the preferred embodiment of the present invention, the above-mentioned counter-ion salt is one or more combinations of sodium salicylate, potassium chloride, carboxy benzene sulfonate, sodium benzoate and potassium hydrogen benzoate.

The invention has the following beneficial effects.

The present invention provides the preparation method of the tri-cationic viscoelastic surfactant by using N,N'-dimethyl-1,3-propanediamine, epichlorohydrin and fatty acid amidopropyl dimethylamine, and the clean fracturing fluid including the viscoelastic surfactant. The prepared clean fracturing fluid can keep excellent viscoelasticity at 180° C., and can be used for fracturing stimulation modification of ultra-high temperature oil-gas reservoirs.

The preparation method of the tri-cationic viscoelastic surfactant disclosed by the invention is simple, and the yield of products is greatly improved, generally reaching more than 96%; in addition, the by-products of the reaction are few, and the influence on the performance of products is small.

When preparing the clean fracturing fluid by using the tri-cationic viscoelastic surfactant of the present invention, the dosage of the tri-cationic viscoelastic surfactant is reduced and the cost is reduced. The critical micelle concentration of the surfactant of the present invention is $1-2 \times 10^{-4}$ mol/L, which is 1-2 orders of magnitude lower than that of the traditional single-chain viscoelastic surfactant.

The temperature resistance and the shear resistance of the clean fracturing fluid prepared by the tri-cationic viscoelastic surfactant of the present invention are good. The existing clean fracturing fluid is commonly used in reservoirs at a temperature below 120° C., few of the clean fracturing fluids can reach the temperature of 140° C. with the help of additives, and the use of additives complicates the system and increases the cost. However, the viscosity of the clean fracturing fluid prepared by the tri-cationic viscoelastic surfactant of the present invention remains above 42 mPa·s after being sheared for 80 minutes at the conditions of 180° C. and 170 s$^{-1}$. The rheological property is excellent and no additive is needed.

The clean fracturing fluid of the present invention is simple to prepare. Only the required mass of the tri-cationic viscoelastic surfactant is dissolved in water and then the counter-ion salt with corresponding concentration is added, then the clean fracturing fluid is obtained after uniformly stirring.

DETAILED DESCRIPTION

The principles and characteristics of the present invention are described below with reference to the accompanying drawings. The embodiments are merely used to explain the present invention, and are not intended to limit the scope of the present invention. The preparation methods in the embodiments which do not indicate the specific conditions are usually in accordance with the conventional conditions, or the manufacturer recommended conditions. Reagents or instruments that do not indicate the manufacturer are conventional products that can be purchased in the market.

Embodiment 1

The preparation method of the tri-cationic viscoelastic surfactant in this embodiment is as follows.

Adding 60 mmol of N,N'-dimethyl-1,3-propanediamine into a round bottom flask, using ethanol as solvent, adding 200 mmol of epichlorohydrin and 60 mmol of concentrated hydrochloric acid, refluxing at 60° C. for 6 hours, performing the distillation under reduced pressure after the reaction, and performing the extraction to obtain intermediate A. Dissolving the obtained intermediate A in ethanol, adding 180 mmol erucamide propyl dimethylamine, refluxing for 12 hours at 85° C. and 250 r/min, and distilling under reduced pressure after the reaction to remove the solvent ethanol, thus obtaining a yellowish viscous liquid, i.e., the tri-cationic viscoelastic surfactant.

The critical micelle concentration of the surfactant in this embodiment is $1.44 \times 10^{-4}$ mol/L.

Figure 1:
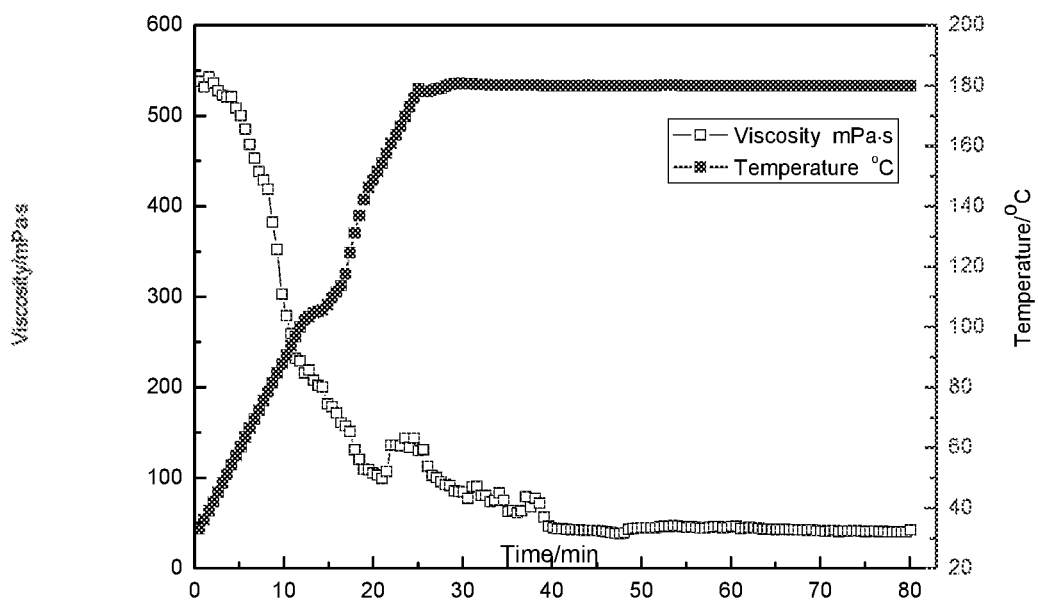
FIG. 1 shows a rheological curve of the clean fracturing fluid prepared by 3% tri-cationic viscoelastic surfactant and 1.2% sodium salicylate of Embodiment 1.
Figure 2:
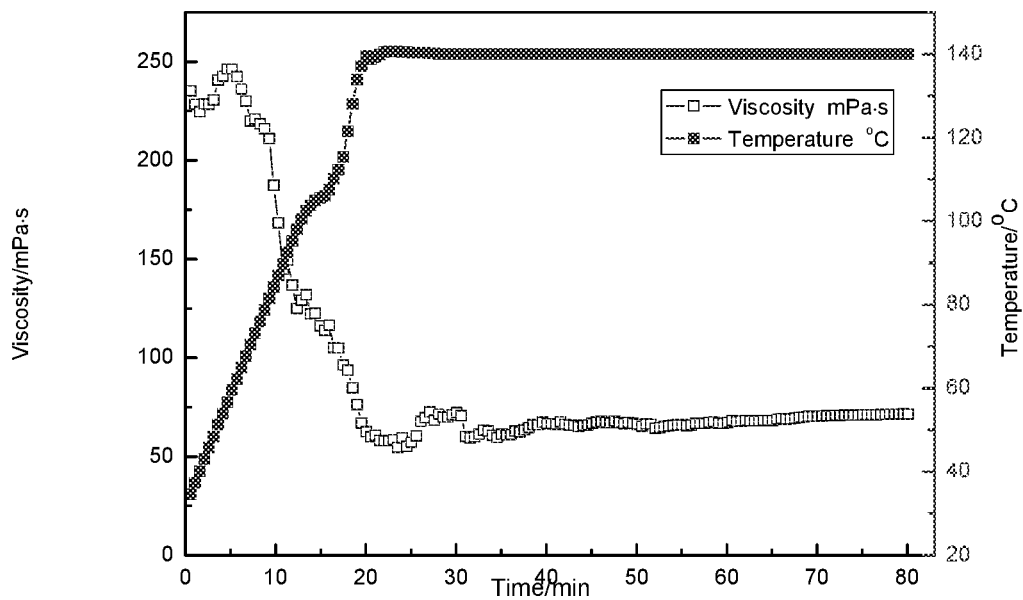
FIG. 2 shows a rheological curve of the clean fracturing fluid prepared by 1% tri-cationic viscoelastic surfactant and 1% sodium salicylate of Embodiment 1.

The rheological properties of the clean fracturing fluids prepared by 3% tri-cationic viscoelastic surfactant and 1.2% sodium salicylate at 180° C. and 170 s$^{-1}$, and 1% tri-cationic viscoelastic surfactant and 1% sodium salicylate at 140° C. and 170 s$^{-1}$ are shown in FIG. 1 and FIG. 2, respectively. The static suspended sand experiment shows that there is no obvious settlement after 2 hours, and the viscosity of the breaking fluid is 3.1 mPa·s after gel breaking with 300% standard formation water.

Embodiment 2

The preparation method of the tri-cationic viscoelastic surfactant in this embodiment is as follows.

Adding 60 mmol of N,N'-dimethyl-1,3-propanediamine into a round bottom flask, using ethanol as solvent, adding 200 mmol of epichlorohydrin and 60 mmol of concentrated hydrochloric acid, refluxing at 60° C. for 6 hours, performing the distillation under reduced pressure after the reaction, and performing the extraction to obtain intermediate A. Dissolving the obtained intermediate A in ethanol, adding 180 mmol oleic amide propyl dimethylamine, refluxing for 12 hours at 85° C. and 270 r/min, and distilling under reduced pressure after the reaction to remove the solvent ethanol, thus obtaining a yellowish viscous liquid, i.e., the tri-cationic viscoelastic surfactant.

The critical micelle concentration of the surfactant in this embodiment is $1.56 \times 10^{-4}$ mol/L.

Figure 3:
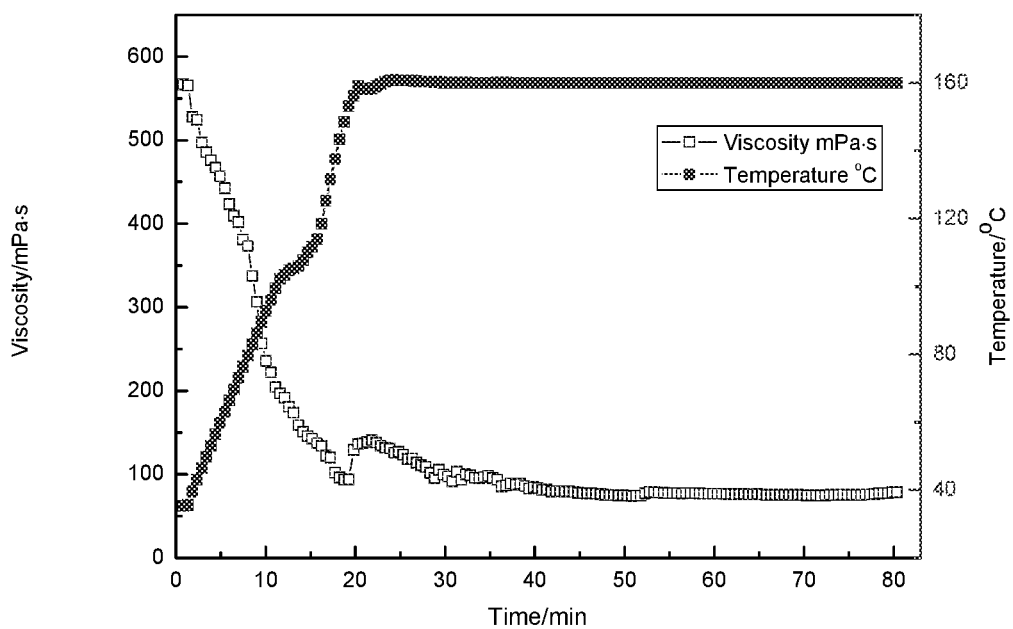
FIG. 3 shows a rheological curve of the clean fracturing fluid prepared by 3% tri-cationic viscoelastic surfactant and 1.4% KCl of Embodiment 2.
Figure 4:
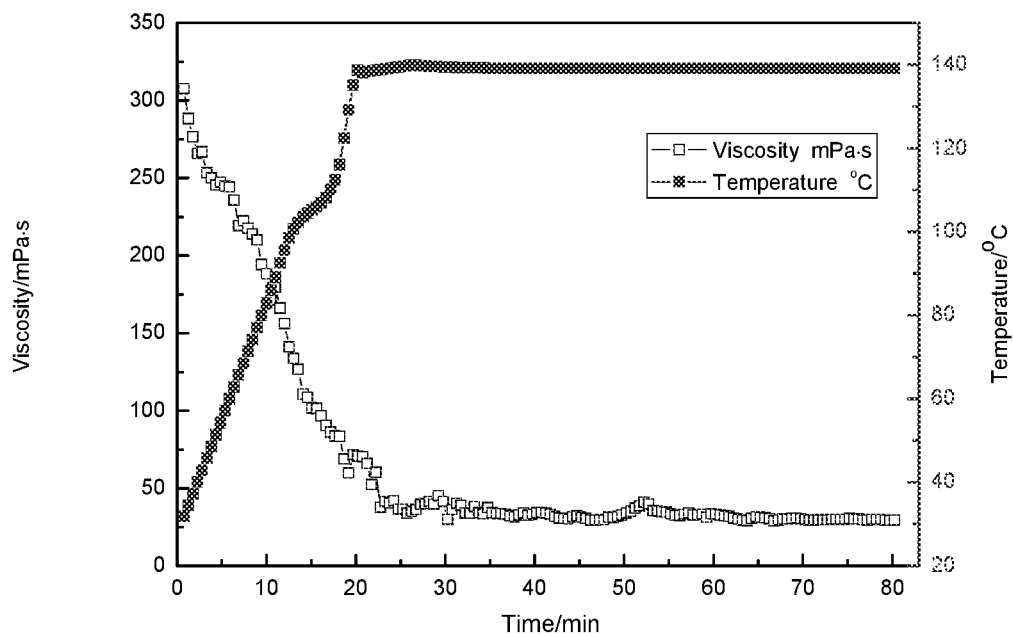
FIG. 4 shows a rheological curve of the clean fracturing fluid prepared by 1% tri-cationic viscoelastic surfactant and 1.2% KCl of Embodiment 2.

The rheological properties of the clean fracturing fluids prepared by 3% tri-cationic viscoelastic surfactant and 1.4% KCl at 160° C. and 170 s$^{-1}$, and 1% tri-cationic viscoelastic surfactant and 1.2% KCl at 140° C. and 170 s$^{-1}$ are shown in FIG. 3 and FIG. 4, respectively. The static suspended sand experiment shows that there is no obvious settlement after 2 hours, and the viscosity of the breaking fluid is 2.8 mPa·s after gel breaking with 300% standard formation water.

Embodiment 3

The preparation method of the tri-cationic viscoelastic surfactant in this embodiment s as follows.

Adding 60 mmol of N,N'-dimethyl-1,3-propanediamine into a round bottom flask, using ethanol as solvent, adding 200 mmol of epichlorohydrin and 60 mmol of concentrated hydrochloric acid, refluxing at 60° C. for 6 hours, performing the distillation under reduced pressure after the reaction, and performing the extraction to obtain intermediate A. Dissolving the obtained intermediate A in ethanol, adding 180 mmol stearic acid amide propyl dimethyl amine, refluxing for 12 hours at 85° C. and 280 r/min, and distilling under reduced pressure after the reaction to remove the solvent ethanol, thus obtaining a yellowish viscous liquid, i.e., the tri-cationic viscoelastic surfactant.

The critical micelle concentration of the surfactant in this embodiment is $1.84 \times 10^{-4}$ mol/L.

Figure 5:
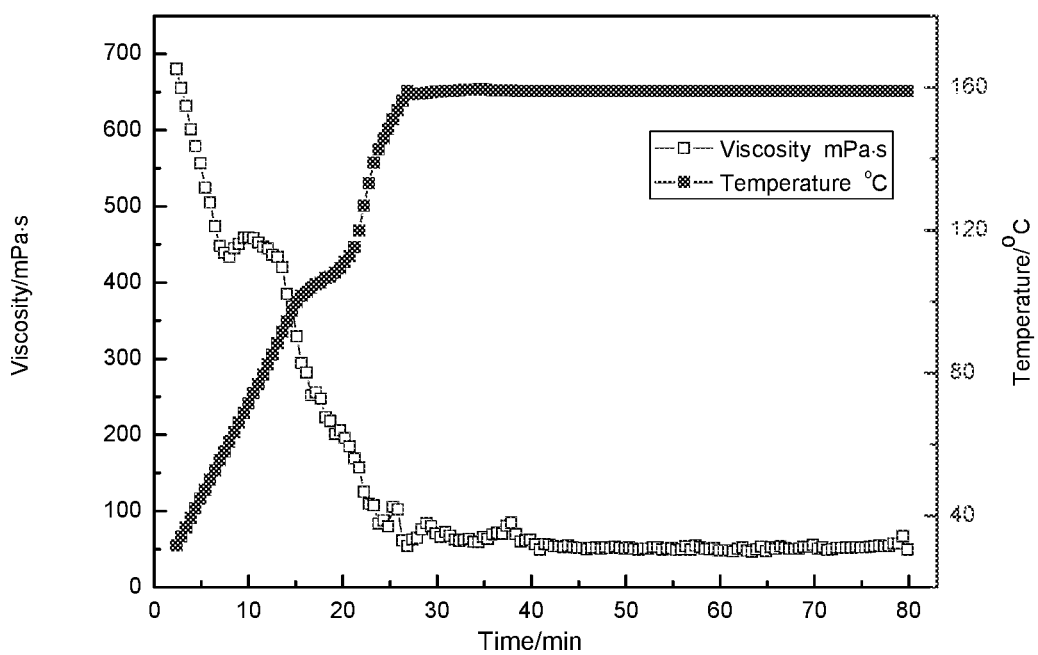
FIG. 5 shows a rheological curve of the clean fracturing fluid prepared by 3% tri-cationic viscoelastic surfactant and 1.2% sodium salicylate of Embodiment 3.
Figure 6:
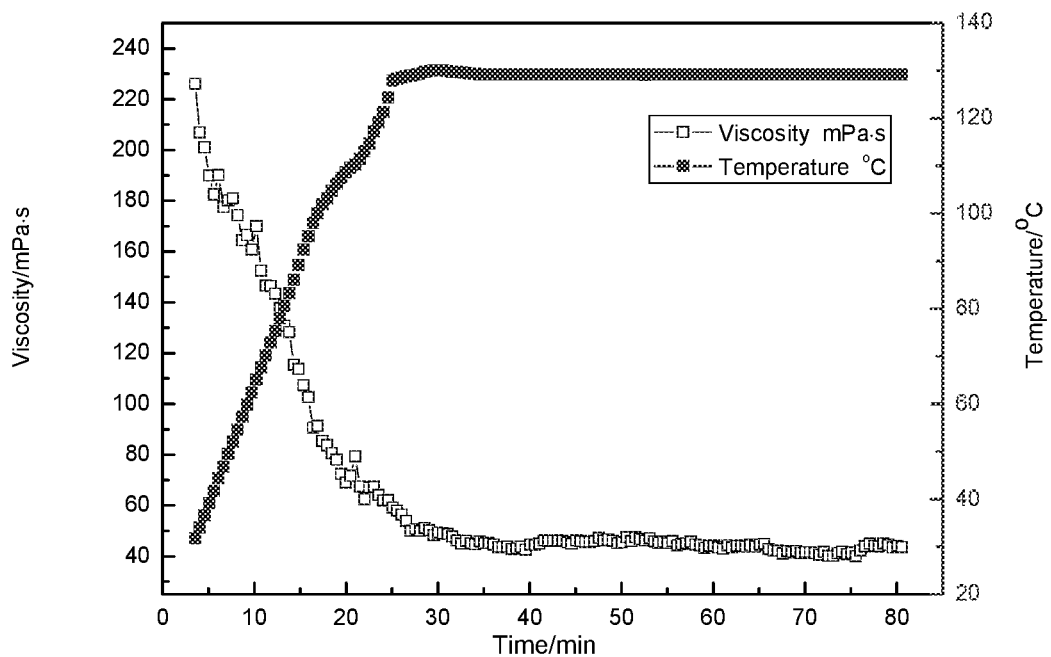
FIG. 6 shows a rheological curve of the clean fracturing fluid prepared by 1% tri-cationic viscoelastic surfactant and 1% sodium salicylate of Embodiment 3.

The rheological properties of the clean fracturing fluids prepared by 3% tri-cationic viscoelastic surfactant and 1.2% sodium salicylate at 160° C. and 170 s$^{-1}$, and 1% tri-cationic viscoelastic surfactant and 1% sodium salicylate at 130° C. and 170 s$^{-1}$ are shown in FIG. 5 and FIG. 6, respectively. The static suspended sand experiment shows that there is no obvious settlement after 2 hours, and the viscosity of the breaking fluid is 2.1 mPa·s after gel breaking with 300% standard formation water.

Embodiment 4

The preparation method of the tri-cationic viscoelastic surfactant in this embodiment is as follows.

Adding 60 mmol of N,N'-dimethyl-1,3-propanediamine into a round bottom flask, using ethanol as solvent, adding 180 mmol of epichlorohydrin and 72 mmol of concentrated hydrochloric acid, refluxing at 55° C. for 7 hours, performing the distillation under reduced pressure after the reaction, and performing the extraction to obtain intermediate A. Dissolving the obtained intermediate A in ethanol, adding 186 mmol stearic acid amide propyl dimethyl amine, refluxing for 13 hours at 80° C. and 300 r/min, and distilling under reduced pressure after the reaction to remove the solvent ethanol, thus obtaining a yellowish viscous liquid, i.e., the tri-cationic viscoelastic surfactant.

Embodiment 5

The preparation method of the tri-cationic viscoelastic surfactant in this embodiment is as follows.

Adding 60 mmol of N,N'-dimethyl-1,3-propanediamine into a round bottom flask, using ethanol as solvent, adding 360 mmol of epichlorohydrin and 90 mmol of concentrated hydrochloric acid, refluxing at 65° C. for 5 hours, performing the distillation under reduced pressure after the reaction, and performing the extraction to obtain intermediate A. Dissolving the obtained intermediate A in ethanol, adding 183 mmol stearic acid amide propyl dimethyl amine, refluxing for 11 hours at 90° C. and 260 r/min, and distilling under reduced pressure after the reaction to remove the solvent ethanol, thus obtaining a yellowish viscous liquid, i.e., the tri-cationic viscoelastic surfactant.

It should be noted that the fatty acid amidopropyl dimethylamine used in the embodiment of the present invention may be any two combinations of erucamide propyl dimethylamine, oleic amide propyl dimethylamine and stearic amide propyl dimethylamine, or the combination of erucamide propyl dimethylamine, oleic amide propyl dimethylamine and stearic amide propyl dimethylamine, in addition to the single components mentioned above. The counter-ion salt used in the embodiment of the present invention may also be any two, three, four or five combinations of sodium salicylate, potassium chloride, carboxy benzene sulfonate, sodium benzoate and potassium hydrogen benzoate.

FIGS. 1-6 show rheological curves of the clean fracturing fluids prepared by the tri-cationic viscoelastic surfactants in the above-mentioned Embodiments 1-3. From the figures, it can be seen that the comparison of FIGS. 1, 3 and 5, and the comparison of FIGS. 2, 4 and 6 both illustrate a problem that when the dosages of the thickening agent are the same and the counter-ion is in the best dosage, the temperature resistance of erucic acid is the best. The temperature resistance of erucic acid with the same dosage in FIGS. 1, 3 and 5 can reach 180° C., and the viscosity of stearic acid is the lowest under the same conditions. Similarly, erucic acid and oleic acid can withstand temperature up to 140° C. at the same dosage in FIGS. 2, 4 and 6, but the viscosity of oleic acid is relatively low. Generally speaking, the clean fracturing fluid of the present invention has high temperature resistance, and the viscosity of the product can be maintained at 42 mPa·s after 80 minutes at 130° C. and 170 s$^{-1}$, which is higher than the viscosity requirement (>25 mPa·s) of the clean fracturing fluid for on-site operation.

Figure 7:
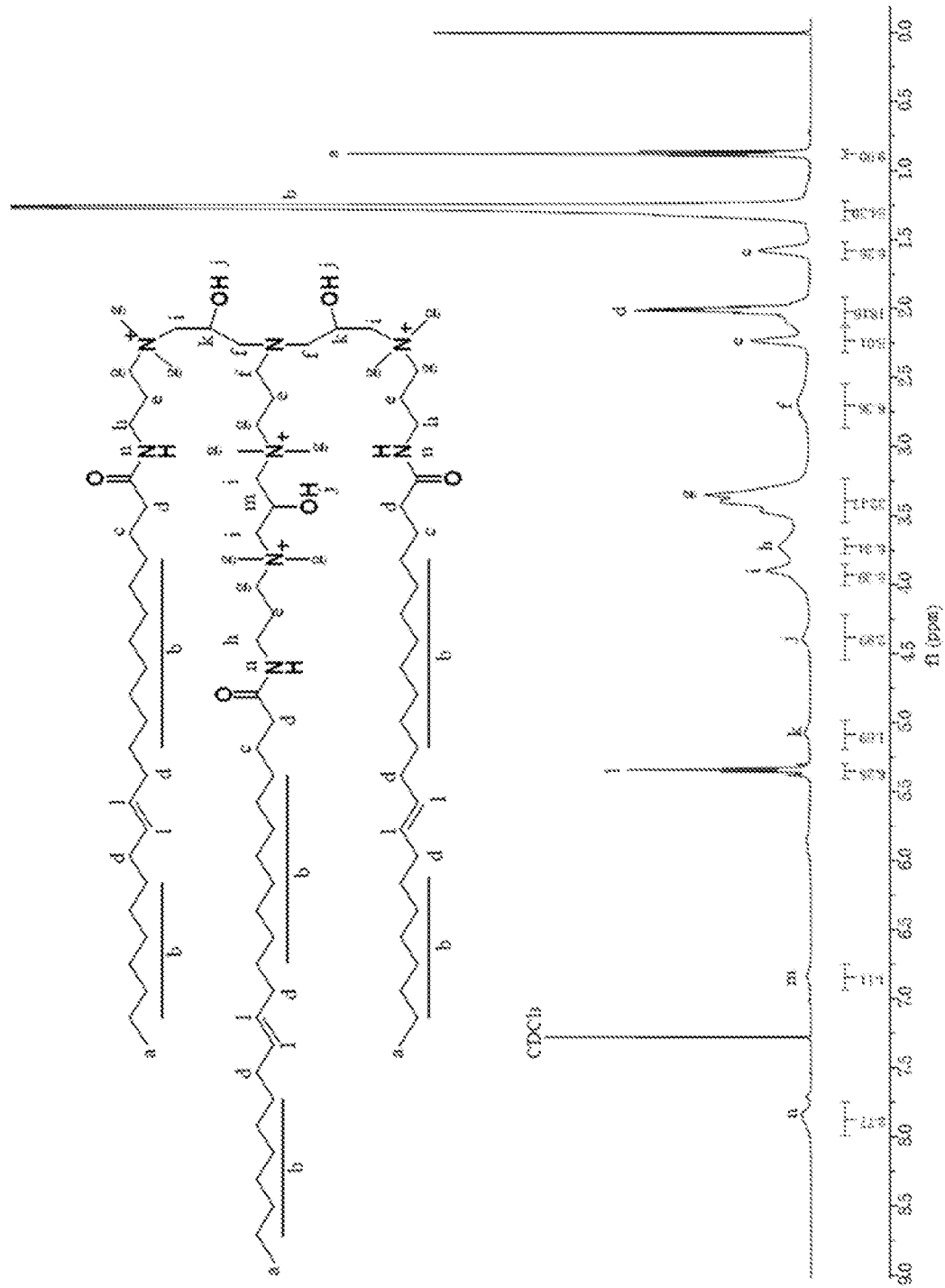
FIG. 7 is a nuclear magnetic resonance spectra diagram of the erucic acid type tri-cationic viscoelastic surfactant of the present invention.

FIG. 7 is a nuclear magnetic resonance spectra diagram of erucic acid type tri-cationic viscoelastic surfactant according to an embodiment of the present invention, which determines the molecular structure of the tri-cationic viscoelastic surfactant.

In summary, the tri-cationic viscoelastic surfactant and the clean fracturing fluid including the surfactant have excellent temperature and shear resistance, good prop-carrying capacity, easy preparation, automatic gel breaking, low damage to formation and low cost. The clean fracturing fluid including the surfactant also has high temperature resistance, and the viscosity of the product can be maintained at 42 mPa·s after 80 minutes at 130° C. and 170 s$^{-1}$, which is higher than the viscosity requirement (>2.5 mPa·s) of the clean fracturing fluid in on-site construction.

The above-mentioned embodiments are merely preferred embodiments of the present invention and are not intended to limit the present invention. Any modifications, equivalents and improvements without departing from the spirit and principle of the present invention shall fall within the scope of the present invention.

What is claimed is:

1. A tri-cationic viscoelastic surfactant, comprising a following structure:

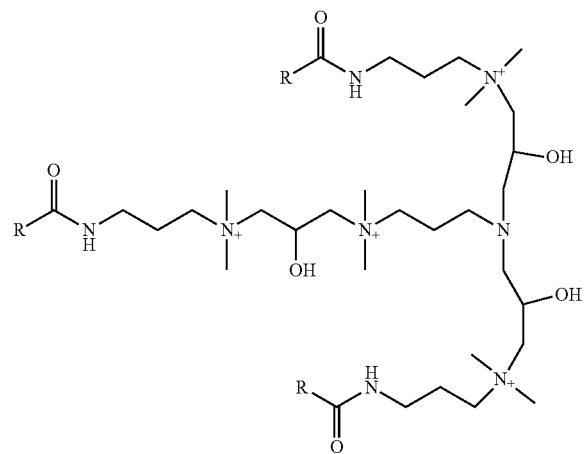

wherein R is a saturated hydrocarbon chain with 17 to 21 carbon atoms or an unsaturated hydrocarbon chain with 17 to 21 carbon atoms.

2. The tri-cationic viscoelastic surfactant according to claim 1, wherein the R is a hydrophobic carbon chain of erucic acid, oleic acid or stearic acid.

3. A preparation method of the tri-cationic viscoelastic surfactant according to claim 1, comprising:
   (1) dissolving N, N'-dimethyl-1,3-propanediamine in an organic solvent, adding epichlorohydrin and concentrated hydrochloric acid, performing a reflux reaction for 5-7 hours at 55-65° C., and then performing a distillation under reduced pressure and performing an extraction to obtain an intermediate A; wherein a molar ratio of the N, N'-dimethyl-1,3-propanediamine to the epichlorohydrin to the concentrated hydrochloric acid is 1:(3-6):(1-1.5);
   (2) dissolving the intermediate A in the organic solvent, adding fatty acid amidopropyl dimethylamine, stirring and performing the reflux reaction for 11-13 h at 80-90° C. and 250-300 r/min, and then performing the distillation under reduced pressure to obtain the tri-cationic viscoelastic surfactant; a molar ratio of intermediate A to the fatty acid amidopropyl dimethylamine is 1:(3-3.1).

4. The preparation method of the tri-cationic viscoelastic surfactant according claim 3, comprising:
   (1) dissolving N, N'-dimethyl-1,3-propanediamine in ethanol, adding epichlorohydrin and concentrated hydrochloric acid, performing the reflux reaction at 60° C. for 6 hours, and then performing the distillation under reduced pressure and performing the extraction to obtain the intermediate A; wherein the molar ratio of the N, N'-dimethyl-1,3-propanediamine to the epichlorohydrin to the concentrated hydrochloric acid is 1:3.3:1;
   (2) dissolving the intermediate A in ethanol, adding the fatty acid amidopropyl dimethylamine, stirring and performing the reflux reaction for 12 h at 85° C. and 250-300 r/min, and then performing the distillation under reduced pressure to obtain the tri-cationic viscoelastic surfactant; the molar ratio of intermediate A to the fatty acid amidopropyl dimethylamine is 1:3.

5. The preparation method of the tri-cationic viscoelastic surfactant according to claim 3, wherein the fatty acid amidopropyl dimethylamine is a combination of one or more of erucamide propyl dimethylamine, oleic amide propyl dimethylamine and stearic amidopropyl dimethylamine.

6. The preparation method of the tri-cationic viscoelastic surfactant according to claim 3, wherein the organic solvent is ethanol or isopropanol.

7. A preparation method of a clean fracturing fluid, comprising the step of using the tri-cationic viscoelastic surfactant according to claim 1 in preparing the clean fracturing fluid and adding the tri-cationic viscoelastic surfactant into water to obtain the clean fracturing fluid.

8. A clean fracturing fluid, comprising: a counter-ion salt and the tri-cationic viscoelastic surfactant of claim 1.

9. The clean fracturing fluid according to claim 8, wherein the clean fracturing fluid comprises 1-3 wt % of the tri-cationic viscoelastic surfactant, 1-1.4 wt % of the counter-ion salt and a rest of the clean fracturing fluid is water.

10. The clean fracturing fluid according to claim 8, wherein the counter-ion salt is one or more combinations of sodium salicylate, potassium chloride, carboxy benzene sulfonate, sodium benzoate and potassium hydrogen benzoate.

11. The preparation method of the clean fracturing fluid according to claim 7, wherein the R is a hydrophobic carbon chain of erucic acid, oleic acid or stearic acid.

12. The preparation method of the clean fracturing fluid according to claim 7, wherein the tri-cationic viscoelastic surfactant is obtained by a process comprising the following steps:
   (1) dissolving N, N'-dimethyl-1,3-propanediamine in an organic solvent, adding epichlorohydrin and concentrated hydrochloric acid, performing a reflux reaction for 5-7 hours at 55-65° C., and then performing a distillation under reduced pressure and performing an extraction to obtain an intermediate A; wherein a molar ratio of the N, N'-dimethyl-1,3-propanediamine to the epichlorohydrin to the concentrated hydrochloric acid is 1:(3-6):(1-1.5);
   (2) dissolving the intermediate A in the organic solvent, adding fatty acid amidopropyl dimethylamine, stirring and performing the reflux reaction for 11-13 h at 80-90°

C. and 250-300 r/min, and then performing the distillation under reduced pressure to obtain the tri-cationic viscoelastic surfactant; a molar ratio of intermediate A to the fatty acid amidopropyl dimethylamine is 1:(3-3.1).

13. The preparation method of the clean fracturing fluid according to claim 12, wherein the tri-cationic viscoelastic surfactant is obtained by a process comprising the following steps:
(1) dissolving N, N'-dimethyl-1,3-propanediamine in ethanol, adding epichlorohydrin and concentrated hydrochloric acid, performing the reflux reaction at 60° C. for 6 hours, and then performing the distillation under reduced pressure and performing the extraction to obtain the intermediate A; the molar ratio of the N, N'-dimethyl-1,3-propanediamine to the epichlorohydrin to the concentrated hydrochloric acid is 1:3.3:1;
(2) dissolving the intermediate A in ethanol, adding the fatty acid amidopropyl dimethylamine, stirring and performing the reflux reaction for 12 h at 85° C. and 250-300 r/min, and then performing the distillation under reduced pressure to obtain the tri-cationic viscoelastic surfactant; the molar ratio of intermediate A to the fatty acid amidopropyl dimethylamine is 1:3.

14. The preparation method of the clean fracturing fluid according to claim 12, wherein the fatty acid amidopropyl dimethylamine is a combination of one or more of erucamide propyl dimethylamine, oleic amide propyl dimethylamine and stearic amidopropyl dimethylamine.

15. The preparation method of the clean fracturing fluid according to claim 12, wherein the organic solvent is ethanol or isopropanol.

* * * * *